United States Patent [19]

Bates

[11] Patent Number: 5,078,686
[45] Date of Patent: Jan. 7, 1992

[54] SINGLE-USE SYRINGE

[76] Inventor: William T. D. Bates, Havenwood, Byfield Road, Charwelton, Daventry, Northants, England

[21] Appl. No.: 369,991

[22] Filed: Jun. 23, 1989

[30] Foreign Application Priority Data

Jun. 28, 1988 [GB] United Kingdom ............... 8815355

[51] Int. Cl.$^5$ ............................................. A61M 5/00
[52] U.S. Cl. ........................... 604/110; 604/218; 604/228; 128/919
[58] Field of Search .............. 604/110, 263, 218, 220, 604/228, 229; 128/919

[56] References Cited

U.S. PATENT DOCUMENTS

| 1,973,308 | 11/1990 | Borras et al. | 604/110 |
|---|---|---|---|
| 2,660,168 | 11/1953 | Pontius | 604/228 |
| 4,391,272 | 7/1983 | Staempfli | 604/110 |
| 4,493,703 | 1/1985 | Butterfield | 604/110 |
| 4,657,028 | 4/1987 | Rich et al. | 128/765 |
| 4,713,056 | 12/1987 | Butterfield | 604/110 |
| 4,878,899 | 11/1989 | Plouff | 604/110 |
| 4,883,466 | 11/1989 | Glazier | 604/110 |
| 4,911,695 | 3/1990 | Lindner | 604/228 |
| 4,915,692 | 4/1990 | Verlier | 604/110 |
| 4,932,941 | 6/1990 | Min et al. | 604/110 |
| 4,950,240 | 8/1990 | Greenwood et al. | 604/110 |
| 4,950,243 | 8/1990 | Estruch | 604/110 |
| 4,973,309 | 11/1990 | Sultan | 604/110 |
| 4,986,812 | 1/1991 | Perler | 604/110 |
| 5,000,735 | 3/1991 | Whelan | 604/110 |

FOREIGN PATENT DOCUMENTS

| 321414 | 6/1989 | European Pat. Off. | 604/110 |
|---|---|---|---|
| 340899 | 11/1989 | European Pat. Off. | 604/110 |
| 1500009 | 9/1966 | France | 604/110 |
| 8802640 | 4/1988 | World Int. Prop. O. | 604/110 |

Primary Examiner—C. Fred Rosenbaum
Assistant Examiner—Mark O. Polutta
Attorney, Agent, or Firm—Oblon, Spivak, McClelland, Maier & Neustadt

[57] ABSTRACT

A single-use syringe has a piston assembly having a plunger (1) with a divergently tapered end portion (4). A resiliently deformable piston (2), with a blind aperture (7) correspondingly tapered so that part of the plunger end portion (4) may fit within, also has a tapered skirt portion (6) adapted to surround a further part of the end portion (4). A locking ring (3) having a tapered aperture to surround said skirt portion is provided to hold the skirt (6) against the plunger end portion (4). When the plunger (1) is depressed within a barrel, the locking ring (3) is delayed by the wall of the barrel while the skirt (6) is pushed inwardly. Once the skirt (6) is unrestrained by the locking ring (3), outward movement of the plunger (1) will cause its end portion (4) to be pulled free from the piston (2). The piston (2) is thus non-retractible to prevent a second drawing in of liquid.

8 Claims, 2 Drawing Sheets

SINGLE-USE SYRINGE

The present invention relates to a single-use syringe.

One important factor in the transmission of certain diseases, most importantly aids, which can be transmitted through blood to blood contact, is the reuse of needles or syringes. Thus, a needle once used by a person infected with the aids virus is contaminated but may be used by some other person who thereby becomes infected. This is particularly true of drug abusers but may also be the case in other areas.

It is an object of the present invention to provide a single-use syringe of a type which cannot be used a second time and therefore cannot contribute to the spread of such diseases.

According to the present invention there is provided a single-use syringe comprising a piston assembly having a plunger with a divergently tapered end portion, a resiliently deformable piston having a blind aperture so correspondingly tapered that part of the plunger end portion may fit therewithin, said piston having a tapered skirt portion adapted to surround a further part of the plunger end portion, and a locking ring having a tapered aperture to surround said skirt portion.

Preferably said locking ring is a split ring.

The taper may comprise an angle in the region of between 1 and 10 degrees, preferably, 1.5 to 5 degrees or, even better, 2 degrees.

An embodiment of the invention will now be more particularly described by way of example and with reference to the accompanying drawings, in which.

Figure 1:
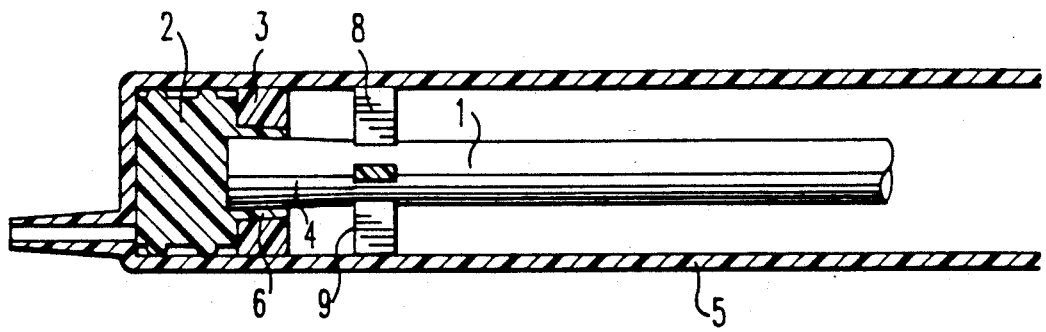
FIG. 1 shows schematically an end of the syringe with the piston assembly in an initial position prior to withdrawal.

A syringe comprises a conventional barrel 5 into which fits a piston assembly. As manufactured, the piston assembly is located at a fully inward disposition, i.e. immediately adjacent the closed end of a syringe barrel.

The piston assembly comprises a plunger 1 having an end 4 which tapers divergently at an angle in the region of 2 degrees. A piston 2 is of a resilient material such as rubber and forms a sliding sealing fit within the barrel 5. The piston 2 has a blind aperture 7 to accommodate an end of the tapered end portion 4 of the plunger 1. Furthermore, a skirt 6, integral with the piston 2 surrounds the blind aperture 7 and continues the taper.

A locking ring 3, which is preferably a split ring of nylon or PVC or the like surrounds the skirt 6. The aperture in the locking ring is correspondingly tapered to surround the skirt 6. The locking ring 3 is in frictional engagement with the internal surface of the barrel 5.

Figure 2:
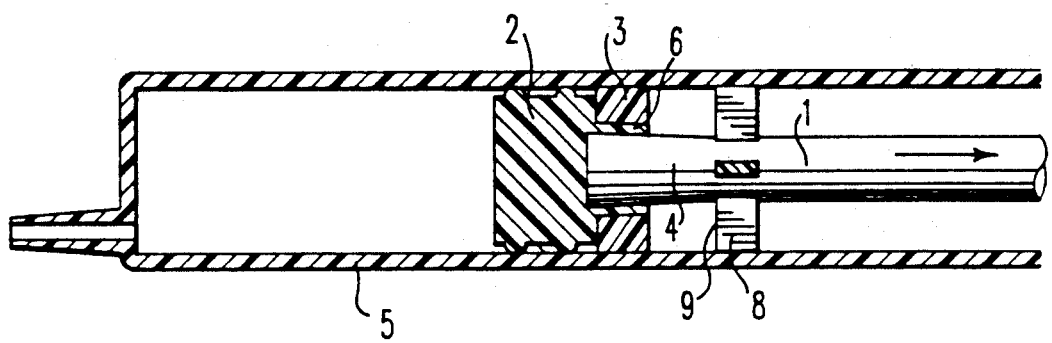
FIG. 2 shows the syringe of FIG. 1 during the piston withdrawal stroke.

As can be seen from FIG. 1, the piston assembly in its initial position is in assembled condition. As the piston assembly is withdrawn (see FIG. 2) to introduce fluid into the syringe, the assembly remains in this condition, the locking ring 3 forcing the skirt 6 to grip the tapered end portion 4 of the plunger 1.

Figure 3:
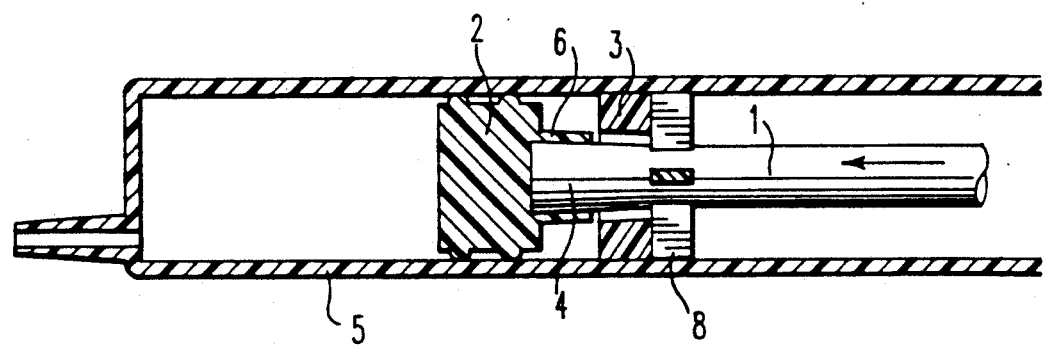
FIG. 3 shows the syringe during the injection stroke.
Figure 4:
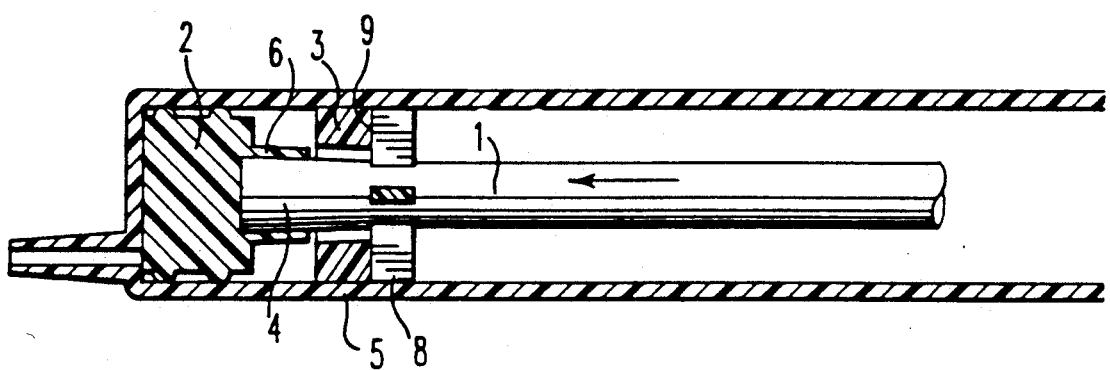
FIG. 4 shows the syringe at the end of the injection stroke.
Figure 5:
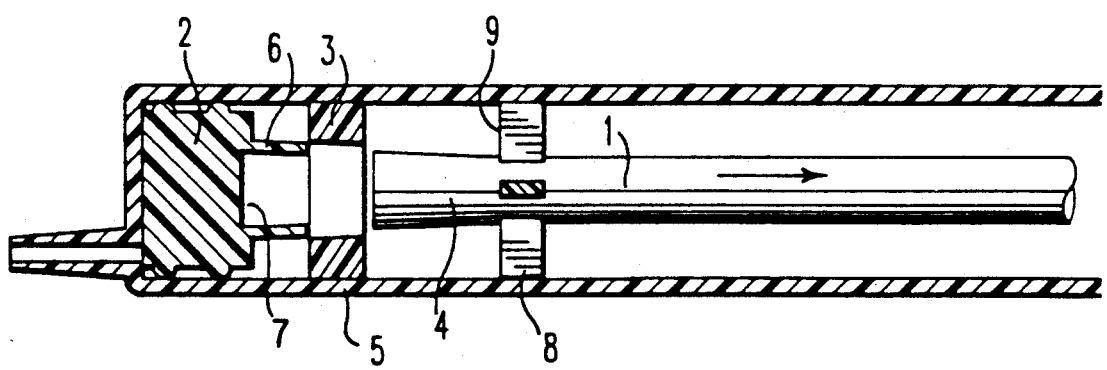
FIG. 5 shows the syringe during a subsequent attempted withdrawal stroke.

On the injection stroke (see FIG. 3) the locking ring is held by its frictional engagement with the barrel while the end portion 4 of the plunger 1 forces the piston 2 inwardly. The locking ring 3 remains behind and thus becomes disengaged from the skirt 6. This condition is maintained until the end of the injection stroke (see FIG. 4).

If an attempt is made to use the syringe a second time, withdrawal of the plunger 1 causes the tapered end portion 4 thereof to become disengaged from the resilient piston 2, since the skirt 6 deforms to allow passage of the tapered end portion. Thus, the piston 2 remains at an innermost position. The plunger is provided with radially extending guide means 8 in sliding engagement with the interior of the barrel and having an inner face 9 which, when the end of the plunger is in locking engagement with the ring 3, is spaced from the rear face of the piston a distance greater than the axial width of the ring so that even if the plunger is forced inwardly, the locking ring 3 cannot be re-engaged around the skirt 6 without a special tool, and therefore the syringe cannot be reused.

During assembly of the syringe, the piston assembly is inserted into the barrel 5 in what is effectively an injection stroke. Normally, this would disengage the locking ring 3 from the skirt 6, and therefore it must be held in position during insertion. This can be achieved quite easily providing the plunger 1 or the guide means 8 does not occupy the whole area of the barrel 5. A cruciform cross-section for the plunger or guide means providing passage means to opposite sides of the guide means 8 would be appropriate. In such a case, a mandrel comprising two rods could be placed alongside the plunger 1 and inserted with it to hold the locking ring 3 in position. A split locking ring 3 is preferred since this renders assembly easier.

I claim:

1. A single use syringe comprising:
   a. a barrel having cylindrical, smooth interior surface;
   b. a piston having front and rear faces and a sliding fluid tight fit with the interior surface of said barrel;
   c. a deformable skirt portion extending rearwardly from the rear face of said piston with its inner surface converging rearwardly;
   d. a manually movable plunger in said barrel rearwardly of said piston, said plunger having a diverging end portion adapted to be received within said skirt portion, and
   e. a separable locking ring in frictional engagement with the interior surface of said barrel and surrounding said skirt portion to retain it in locking engagement with the diverging end portion of said plunger to enable said piston to be retracted in said barrel when said plunger is manually moved in an outward direction;
   f. the frictional engagement of said locking ring with the internal surface of said barrel being of a magnitude that when said plunger is moved inwardly in a fluid injecting direction said locking ring remains behind until said skirt portion is clear of said locking ring whereupon subsequent movement of said plunger in an outward direction frees it from said piston and the latter cannot be retracted for further use of the syringe.

2. The single use syringe of claim 1 including radially extending guide means carried by said plunger and in sliding engagement with the interior surface of said barrel, said guide means having an inner face spaced from the rear face of said piston, when the end of said plunger is in locking engagement with said ring, a distance greater than the axial width of said ring whereby on a second inward movement of said plunger said guide means is incapable of moving said ring back to a locking position.

3. The single use syringe of claim 1 wherein said piston is also resiliently deformable, said piston having on its outer face an internally tapered blind bore to accommodate an end part of said plunger.

4. A syringe as claimed in claim 1, wherein said locking ring is a split ring.

5. A syringe as claimed in claim 1, wherein the angle of taper is in the region of between 1° and 10° with respect to the longitudinal axis of the plunger.

6. A syringe as claimed in claim 5, wherein the angle of taper is in the region of 1.5 to 5.0°.

7. A syringe as claimed in claim 6, wherein the angle of taper is in the region of 2°.

8. A syringe as claimed in claim 2 including passage means extending entirely through said guide means and being of a size to accommodate elongate members for maintaining said locking ring in engagement with said skirt portion during initial assembly of said syringe prior to use.

* * * * *